United States Patent [19]
Cottrell et al.

[11] Patent Number: 5,260,571
[45] Date of Patent: Nov. 9, 1993

[54] METHOD OF PREPARING A SAMPLE FOR ANALYSIS

[75] Inventors: John S. Cottrell, London, United Kingdom; Kuldip K. Mock, Sunnyvale, Calif.

[73] Assignee: Finnigan MAT Limited, Hemel Hempstead Herts, United Kingdom

[21] Appl. No.: 835,970
[22] PCT Filed: Jun. 25, 1990
[86] PCT No.: PCT/GB90/00974
§ 371 Date: Feb. 20, 1992
§ 102(e) Date: Feb. 20, 1992
[87] PCT Pub. No.: WO91/02961
PCT Pub. Date: Mar. 7, 1991

[30] Foreign Application Priority Data

Jun. 23, 1989 [GB] United Kingdom ............... 8919193

[51] Int. Cl.$^5$ .............................................. H01J 44/04
[52] U.S. Cl. ...................................... 250/288; 250/282
[58] Field of Search ................ 250/288, 288 A, 282, 250/281; 436/124, 125, 173

[56] References Cited

U.S. PATENT DOCUMENTS

| | | | |
|---|---|---|---|
| 4,874,944 | 10/1989 | Kato | 250/288 |
| 4,920,264 | 4/1990 | Becker | 250/288 |
| 4,988,879 | 1/1991 | Zare et al. | 250/288 |
| 5,045,694 | 9/1991 | Beavis et al. | 250/282 |
| 5,077,470 | 12/1991 | Cody et al. | 250/288 |
| 5,118,937 | 6/1992 | Hillenkamp et al. | 250/288 |
| 5,135,870 | 8/1992 | Williams et al. | 250/288 |
| 5,146,088 | 9/1992 | Kingham et al. | 250/288 |

FOREIGN PATENT DOCUMENTS

| | | |
|---|---|---|
| 62-43562 | 2/1987 | Japan. |
| 62-284256 | 10/1987 | Japan. |
| 8701452 | 3/1987 | PCT Int'l Appl.. |
| 2187327 | 9/1987 | United Kingdom. |

OTHER PUBLICATIONS

Davis et al., "Identification of Naturally Occurring Quaternary Compounds by Combined Laser Desorption and Tandem Mass Spectrometry", Analytical Chemistry, vol. 55 No. 8, (Jul. 1983), pp. 1302-1305.

Karas et al., "Matrix Assisted Ultrviolet Laser Desorption of Non-volatile Compounds," International Journal of Mass Spectrometry and Ion Processes, vol. 78 (1987), pp. 53-68.

Shomo et al., "Laser Desorption Fourier Transform Ion Cyclotron Resonance Mass Spectrometry vs. Fast Atom Bombardment Magnetic Sector Mass Spectrometry for Drug Analysis," Analytical Chemistry, vol. 57 No. 14 (1985), pp. 2940-2944.

Wright et al., "Matrix Enhanced Laser Desorption in Mass Spectrometry and Tandem Mass Spectrometry", Biomedical Mass Spectrometry, vol. 12, No. 4 (1985), pp. 159-162.

Primary Examiner—Paul M. Dzierzynski
Assistant Examiner—Kiet T. Nguyen
Attorney, Agent, or Firm—Flehr, Hohbach, Test, Albritton & Herbert

[57] ABSTRACT

A sample for analysis by Laser Desorption Mass Spectrometry is prepared by applying a substrate material to a target for the mass spectrometer, dissolving the sample material in a solvent and applying the solution to a substrate material on the target to be absorbed thereby. A matrix material is also dissolved in a solvent and this matrix material in solution is applied to the substrate material on the target. The solvent used to dissolve the matrix material is chosen such as to release the sample material from the substrate so that, after evaporation of the matrix material, there is provided on the substrate material an intimately mixed deposit of sample material and matrix material.

7 Claims, 1 Drawing Sheet

METHOD OF PREPARING A SAMPLE FOR ANALYSIS

FIELD OF THE INVENTION

This invention relates to a method of preparing a sample for analysis, and particularly a sample for analysis by Laser Desorption Mass Spectrometry (LDMS) in which ions are sputtered from a condensed phase sample surface by photon bombardment and are then subjected to mass analysis.

BACKGROUND OF THE INVENTION

Many methods of LDMS are known, and a feature common to many is the use of a matrix material in which the analyte (the sample material to be analysed) is dispersed. The matrix material can serve one or more of a plurality of functions. For example it may act as a mediator in transferring energy from the photon bombardment to the sample material molecules; it may provide a physical and chemical environment which enhances the probability of desorption in the desired state of charge and aggregation; and it may remove excess energy from the desorbed species through evaporation of matrix material molecules from a desorbed cluster of sample material and matrix material ions.

Four techniques for using a matrix material to enhance LDMS have been described as set out below.

The first is to dissolve the sample material together with a 10:1 excess of an inorganic salt in a solvent, place a drop of the solution on the target surface, and evaporate to dryness as described by D. V. Davis et. al. in Analytical Chemistry, 55 1302 (1983). The sample material deposit is then irradiated with infra-red photons from a pulsed Neodymium YAG laser.

The second is to mix equimolar amounts of sample material and an inorganic salt in a droplet of glycerol placed on the target surface as described by L. G. Wright et. al. in Biomedical Mass Spectrometry, 12, 159 (1985). The sample mixture is then irradiated with infra-red photons from a continuous wave carbon dioxide laser.

Thirdly, Japanese Patent Specification JP62-43562 discloses a sample preparation technique in which a solution of the sample material is mixed with a slurry of glycerol and fine cobalt powder. A droplet of the mixture is then irradiated with ultraviolet photons from a pulsed nitrogen laser.

Fourthly, M. Karas et. al. (Int. J. Mass Spectrom. Ion Processes, 78, 53 (1987)) describe using a large molar excess of a matrix material which has a strong absorption at the wavelength of the incident radiation. For example, the sample material is dissolved in a solution containing a thousand-fold molar excess of Nicotinic Acid. A drop of the solution is placed on the target surface, evaporated to dryness, and irradiated with 266 nm ultraviolet photons from a frequency quadrupled pulsed Neodymium YAG laser. The use of a matrix material which has a strong absorption for the incident photons represents an important distinction between this approach and the first three described because it allows the use of low power densities which increases the probability of desorbing intact molecular ions.

SUMMARY OF THE INVENTION

According to this invention there is provided a method of preparing a sample for analysis by laser desorption mass spectrometry, comprising applying a substrate material to a target for the mass spectrometer to be used; dissolving the sample material in a solvent and applying the solution to the substrate material on the target to be absorbed thereby; dissolving a matrix material in a solvent; and applying the matrix material solution to the substrate material on the target, the solvent used to dissolve the matrix material being such as to release the sample material from the substrate material thereby to provide on the substrate material on the target, after evaporation of the matrix material solvent, an intimately mixed deposit of sample material and matrix material.

Preferably the matrix material has a strong absorption for the photon bombardment used for mass spectrometry.

Preferably the substrate material is applied to the target by a technique such as electrospraying which provides a deposit with a large surface area.

BRIEF DESCRIPTION OF THE DRAWINGS

The invention will now be described by way of example with reference to the drawing, in which the two figures illustrate two methods of sample preparation in accordance with the invention.

DETAILED DESCRIPTION OF THE INVENTION

Figure 1:
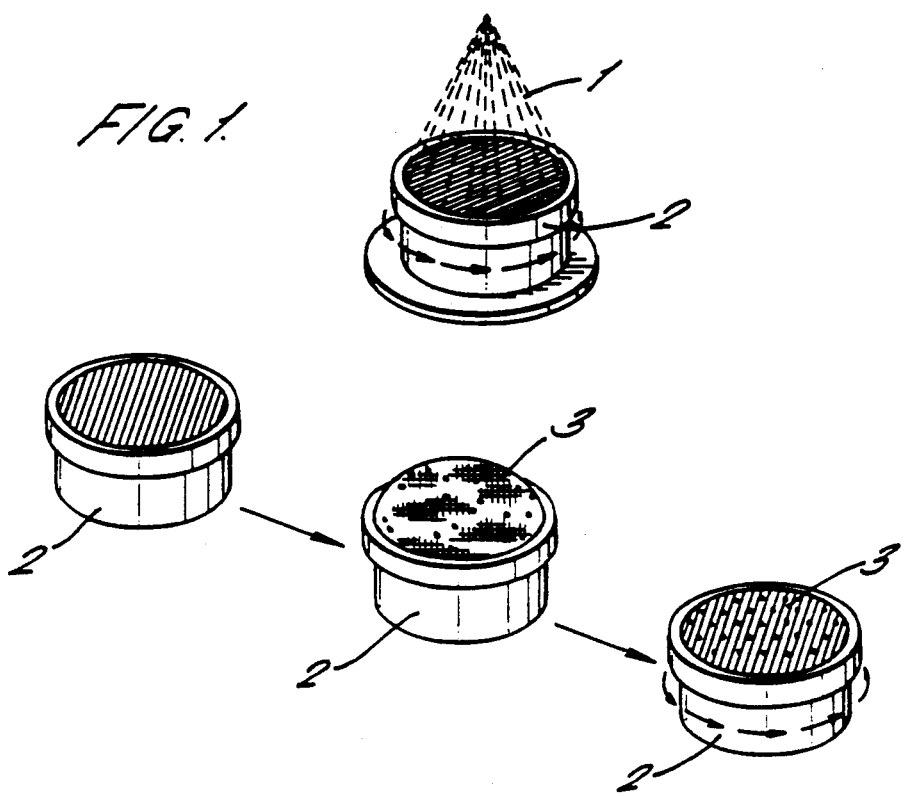
FIG. 1 illustrates the step in carrying out the invention.

Referring to FIG. 1, a substrate material 1, for example Nitrocellulose, is electrosprayed in known manner onto the central region of a rotated target stage 2 of a mass spectrometer. A mask may be used to ensure that the substrate material 1 is restricted to a well defined area of known diameter. The electrospray technique is described fully by C. J. McNeal et. al. in Analytical Chemistry, 51 2036 (1979). A drop of sample material solution 3, for example a $10^{-5}$ molar solution of the peptide in 0.1% aqueous Trifluoroacetic Acid is placed onto the target 2 so as to cover the substrate material deposit. The sample material solution 3 is allowed to remain in contact with the substrate material for a period of several seconds so that the peptide molecules will bind to the Nitrocellulose through hydrophobic interaction. If the solution fails to wet the substrate material surface, a microscope slide cover slip can be placed on top of the droplet so as to encourage it to spread out over the surface. Once the peptide has been immobilised onto the substrate material surface, the droplet can be blown off with compressed gas, spun off, or rinsed off by either a stream of solvent or immersion in bulk solvent. Alternatively, the droplet could simply be allowed to dry out, but this would mean that any contaminants would also be left on the target surface.

The absorbed sample material solution can then be derivatised using a suitable chemical reagent or enzyme.

A droplet of matrix material solution consisting of $3 \times 10^{-2}$ molar Nicotinic Acid in acetone is then applied to the target to cover the sample material deposit. The acetone solvent used for the matrix material will dissolve surface layers of the nitrocellulose substrate material together with the attached peptide molecules, so that sample material and matrix material become intimately mixed in the droplet. The droplet is then allowed to dry naturally by evaporation of the solvent (acetone) or can be assisted to dry by the application of heat or forced air.

The loaded target 2 can then be introduced into the source region of a mass spectrometer for analysis of the sample material by bombardment with 266 nm photons from a frequency quadrupled Neodymium YAG laser, in known manner.

Substrate materials exhibiting highly specific binding properties such as immunoadsorbants can be used.

Figure 2:
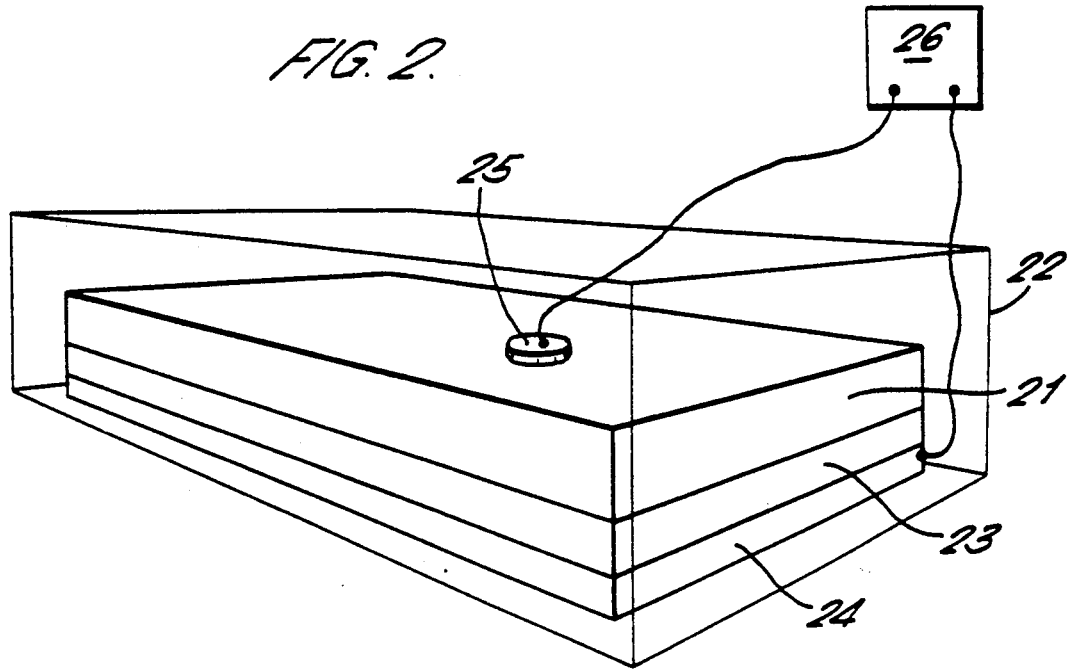
FIG. 2 shows an alternative method of loading sample material onto a target.

Referring now to FIG. 2, an alternative method of loading sample material onto a target with the substrate material thereon is blotting. By this means, sample material may be transferred directly from an electrophoretic or chromatographic support onto a prepared target. The techniques for performing electrophoretic separations and staining are well known to those skilled in the art and descriptions may be found in "Electrophoresis, Theory, Techniques, and Biochemical and Clinical Applications" by A. T. Andrews, Clarendon Press, Oxford, 1986. The techniques for blotting are also well known and are described in "Protein Blotting, Methodology, Research and Diagnostic Applications" edited by B. A. Baldo and E. R. Tovey, Karger, Basel, 1989.

In one embodiment, a mixture of proteins is denatured using sodium dodecyl sulphate and separated electrophoretically in a slab 21 of polyacrylamide gel. The gel is subsequently stained to reveal the positions of the separated components. The gel 21 is placed in a semi-dry blotting tank 22 on a filter paper 23 and a bottom electrode 24 and one or more targets 25 precoated with a substrate material are placed face down on the upper surface of the gel 21 at the locations of the components or interest. The filter paper 23 and the upper surface of the gel 21 are wetted with a solvent of 25 mM Tris, 192 Mm glycine, and 20% (v/v) methanol in water. By applying a potential difference of a few tens of volts from a source 26 between the bottom electrode 24 and the conductive targets 25, proteins are induced to migrate from the gel 21 towards the targets 25 where they are bound by the substrate material. The targets 25 may then be removed, rinsed, the matrix solution added as described previously, dried, and introduced into the source region of a mass spectrometer for analysis by bombardment with 266 nm photons from a frequency quadrupled Neodymium YAG laser.

We claim:

1. A method of preparing a sample for analysis by laser desorption mass spectrometry, comprising applying a substrate material to a target for the mass spectrometer to be used; dissolving the sample material in a solvent and applying the solution to the substrate material on the target to be absorbed thereby; dissolving a matrix material in a solvent; and applying the matrix material solution to the substrate material on the target, the solvent used to dissolve the matrix material being such as to release the sample material from the substrate material thereby to provide on the substrate material on the target, after evaporation of the matrix material solvent, an intimately mixed deposit of sample material and matrix material.

2. A method as claimed in claim 1, in which the matrix material has a strong absorption for the photon bombardment used for mass spectrometry.

3. A method as claimed in claim 1 in which the substrate material is applied to the target by electrospraying.

4. A method as claimed in claim 1 in which the sample material is applied to the substrate material by blotting.

5. A method as claimed in claim 1 in which the substrate material is Nitrocellulose.

6. A method as claimed in claim 1 in which the substrate material is an immunoadsorbant.

7. A method as claimed in claim 1 in which the sample material is derivatised after application to the substrate material and before application of the matrix material solution.

* * * * *